United States Patent
Inagaki et al.

(10) Patent No.: US 10,242,436 B2
(45) Date of Patent: Mar. 26, 2019

(54) NON-DESTRUCTIVE INSPECTION APPARATUS

(71) Applicants: IHI Corporation, Koto-ku (JP); KEN AUTOMATION, INC., Yokohama-shi (JP)

(72) Inventors: Koichi Inagaki, Tokyo (JP); Kunihiko Takao, Tokyo (JP)

(73) Assignees: IHI Corporation, Koto-ku (JP); KEN AUTOMATION, INC., Yokohama-shi (JP)

( * ) Notice: Subject to any disclaimer, the term of this patent is extended or adjusted under 35 U.S.C. 154(b) by 178 days.

(21) Appl. No.: 15/340,335

(22) Filed: Nov. 1, 2016

(65) Prior Publication Data

US 2017/0046831 A1   Feb. 16, 2017

Related U.S. Application Data

(63) Continuation of application No. PCT/JP2015/067500, filed on Jun. 17, 2015.

(30) Foreign Application Priority Data

Jun. 17, 2014 (JP) .................................. 2014-124497

(51) Int. Cl.
*G06T 7/00* (2017.01)
*G01N 25/72* (2006.01)
(Continued)

(52) U.S. Cl.
CPC .......... *G06T 7/0004* (2013.01); *G01N 25/72* (2013.01); *G06T 7/001* (2013.01); *G06T 7/521* (2017.01);
(Continued)

(58) Field of Classification Search
CPC ...... G01B 11/2441; G06T 7/0006; B22C 7/02
(Continued)

(56) References Cited

U.S. PATENT DOCUMENTS 6,394,646 B1    5/2002  Ringermacher et al.
9,488,470 B1 *  11/2016 Peterson ............ G01B 11/2441
(Continued)

FOREIGN PATENT DOCUMENTS

JP    2003-512596    4/2003
JP    2005-24556     1/2005
(Continued)

OTHER PUBLICATIONS

E. Savio, et al., "Metrology of Freeform Shaped Parts", Annals of the CIRP, vol. 56 No. 2, XP22356750, Nov. 22, 2007, pp. 810-835.
(Continued)

*Primary Examiner* — Tung T Vo
(74) *Attorney, Agent, or Firm* — Oblon, McClelland, Maier & Neustadt, L.L.P.

(57) ABSTRACT

A non-destructive inspection apparatus is configured to perform non-destructive inspection of a bonded place between a base material and a bonding material of a gas turbine engine part formed by bonding the bonding material formed of a metal material to the base material formed of a fiber-strengthened material, and includes a moving apparatus configured to move the gas turbine engine part, a light source apparatus configured to emit a laser beam, an infrared imaging apparatus configured to image the gas turbine engine part to which the laser beam is radiated, and a control and arithmetic processing apparatus configured to store form data of the gas turbine engine part, control the moving apparatus such that the laser beam is radiated to the bonded place based on the form data, and obtain a result showing a (Continued)

state of the bonded place based on imaging data obtained by the infrared imaging apparatus.

5 Claims, 6 Drawing Sheets

(51) Int. Cl.
*H04N 5/225* (2006.01)
*H04N 5/33* (2006.01)
*G06T 7/521* (2017.01)

(52) U.S. Cl.
CPC ............ *H04N 5/2256* (2013.01); *H04N 5/33* (2013.01); *G06T 2207/10048* (2013.01); *G06T 2207/30164* (2013.01)

(58) Field of Classification Search
USPC ........................................................ 348/86
See application file for complete search history.

(56) References Cited

U.S. PATENT DOCUMENTS

| | | | |
|---|---|---|---|
| 2003/0167616 A1 | 9/2003 | Harding et al. | |
| 2004/0262521 A1 | 12/2004 | Devitt et al. | |
| 2007/0217672 A1* | 9/2007 | Shannon | G06T 7/0006 |
| | | | 382/152 |
| 2009/0312956 A1* | 12/2009 | Zombo | F01D 5/288 |
| | | | 702/34 |
| 2012/0219034 A1 | 8/2012 | Nielsen | |
| 2013/0148689 A1 | 6/2013 | Yahaba et al. | |
| 2013/0333855 A1* | 12/2013 | Merrill | B22C 7/02 |
| | | | 164/45 |
| 2014/0286782 A1* | 9/2014 | Mulford | F01D 5/32 |
| | | | 416/220 R |
| 2014/0313324 A1 | 10/2014 | Bienkowski et al. | |

FOREIGN PATENT DOCUMENTS

| | | |
|---|---|---|
| JP | 2009-244021 | 10/2009 |
| JP | 2009-282020 | 12/2009 |
| JP | 2011-506927 | 3/2011 |
| JP | 2011-247735 | 12/2011 |
| JP | 2012-181194 | 9/2012 |
| JP | 2013-122414 | 6/2013 |
| RU | 2 379 645 C2 | 1/2010 |
| WO | WO 2009/073014 A1 | 6/2009 |
| WO | WO 2013/087433 A1 | 6/2013 |

OTHER PUBLICATIONS

International Search Report dated Sep. 8, 2015 in PCT/JP2015/067500, filed on Jun. 17, 2015 ( with English Translation).

Written Opinion dated Sep. 8, 2015 in PCT/JP2015/067500, filed on Jun. 17, 2015.

* cited by examiner

NON-DESTRUCTIVE INSPECTION APPARATUS

This application is a continuation application based on a PCT Patent Application No. PCT/JP2015/067500, filed on Jun. 17, 2015, whose priority is claimed on Japanese Patent Application No. 2014-124497, filed on Jun. 17, 2014. The contents of both the PCT Application and the Japanese Application are incorporated herein by reference.

TECHNICAL FIELD

Embodiments described herein relates to a non-destructive inspection apparatus.

BACKGROUND ART

In the related art, gas turbine engine parts such as blades used in a gas turbine engine are formed of metal materials. In recent times, gas turbine engine parts may be formed by bonding a base material formed of a fiber-strengthened material and a bonding material formed of a metal material for the purpose of reduction in weight or the like. In this case, in order to increase reliability of the parts, states of bonding places between the base material and the bonding material should be inspected and checked.

For example, in Patent Documents 1 to 3, non-destructive inspection methods using laser beams are disclosed.

Incidentally, since gas turbine engine parts have complex three-dimensional shapes and various kinds of parts are used according to use environments, non-destructive inspection at bonding places is not easy. Here, as the non-destructive inspection method with respect to the gas turbine engine parts, a method of inspecting states of bonding places from imaging data by applying a black body tape or a black body paint to inspection target places, radiating light from a flashlamp toward the black body tape or the black body paint and imaging the bonding places using an infrared camera or the like is used.

CITATION LIST

Patent Documents

Patent Document 1: Japanese Unexamined Patent Application, First Publication No. 2011-247735
Patent Document 2: Japanese Unexamined Patent Application, First Publication No. 2009-244021
Patent Document 3: Published Japanese Translation No. 2011-506927 of the PCT International Publication

SUMMARY

However, in the above-mentioned method, work of applying black body tapes or black body paint to the gas turbine engine parts one by one is needed, and a workload is increased. For this reason, a method that enables non-destructive inspection of bonding places of various kinds of gas turbine engine parts having complex shapes to be easily performed without the black body tape or the black body paint being applied is desired.

The present disclosure has been made in view of the above circumstances, and an object thereof is, in non-destructive inspection of a bonding place of a gas turbine engine part in which a bonding material formed of a metal material is bonded to a base material formed of a fiber-strengthened material, to enable inspection of various kinds of gas turbine engine parts having complex shapes to be easily performed without a black body tape or black body paint being applied.

One aspect according to the present disclosure is a non-destructive inspection apparatus configured to perform non-destructive inspection of a bonded place between a base material and a bonding material of a gas turbine engine part, the gas turbine engine part being formed by bonding the bonding material formed of a metal material to the base material formed of a fiber-strengthened material, the non-destructive inspection apparatus including: a moving apparatus configured to move the gas turbine engine part; a light source apparatus configured to emit a laser beam; an infrared imaging apparatus configured to image the gas turbine engine part to which the laser beam is radiated; and a control and arithmetic processing apparatus configured to store form data of the gas turbine engine part, control the moving apparatus such that the laser beam is radiated to the bonded place based on the form data, and obtain a result showing a state of the bonded place based on imaging data obtained by the infrared imaging apparatus.

According to the present disclosure, since laser beam having a higher energy density than a flashlamp is radiated to a bonding place, non-destructive inspection can be performed without applying the black body tape or the black body paint. In addition, the control and arithmetic processing apparatus, which stores form data of the gas turbine engine part, controls the moving apparatus configured to move the gas turbine engine part such that laser beam is radiated to the bonding place. Accordingly, inspection can be easily performed with respect to the various kinds of gas turbine engine parts having complex shapes. As a result, according to the present disclosure, in the non-destructive inspection of the bonding place of the gas turbine engine part in which the bonding material formed of the metal material is bonded to the base material formed of the fiber-strengthened material, the inspection can be easily performed with respect to the various kinds of gas turbine engine parts having complex shapes without applying the black body tape or the black body paint.

DESCRIPTION OF EMBODIMENTS

Hereinafter, an embodiment of a non-destructive inspection apparatus of the present disclosure will be described with reference to the accompanying drawings. In the following drawings, scales of members may be appropriately varied in order for the members to be identifiable.

Figure 1:
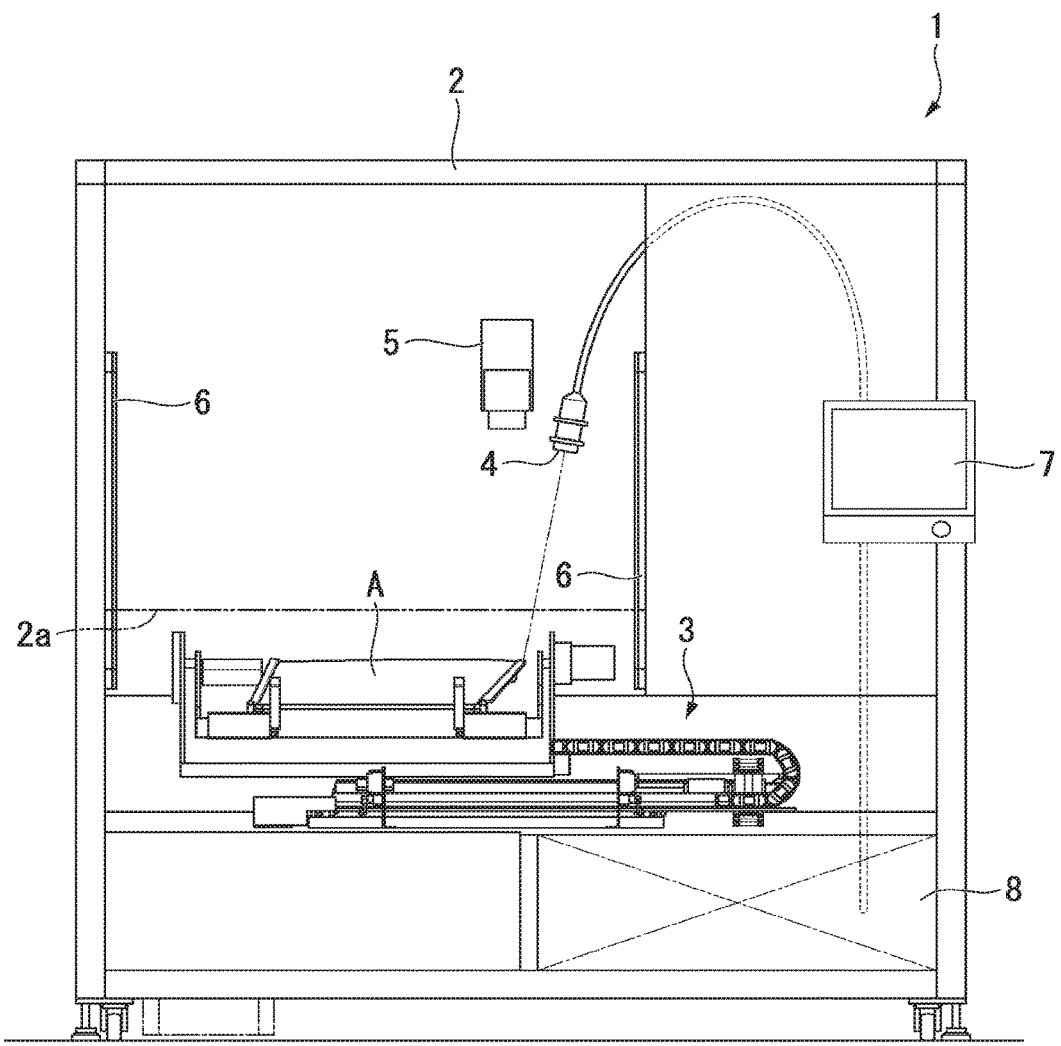
FIG. 1 is a front view showing a schematic configuration of a non-destructive inspection apparatus according to an embodiment of the present disclosure.

FIG. 1 is a front view showing a schematic configuration of a non-destructive inspection apparatus 1. As shown in FIG. 1, the non-destructive inspection apparatus 1 of the embodiment includes a housing 2, a moving apparatus 3, a laser beam source apparatus 4 (a light source apparatus), an infrared camera 5 (an infrared imaging apparatus), a curtain sensor 6, a manipulation monitor 7 and a control unit 8 (a control and arithmetic processing apparatus).

The housing 2 accommodates the moving apparatus 3, the laser beam source apparatus 4, the infrared camera 5, the curtain sensor 6 and the control unit 8. The housing 2 has an opening section through which a guide vane A (a gas turbine engine part) serving as an inspection target is inserted into or ejected from the housing 2. An elevating shutter 2a that is closed upon laser radiation is installed at the opening section. Note that the guide vane A is a guide blade configured to rectify air that exits to the outside from a fan in a gas turbine engine.

Figure 2:
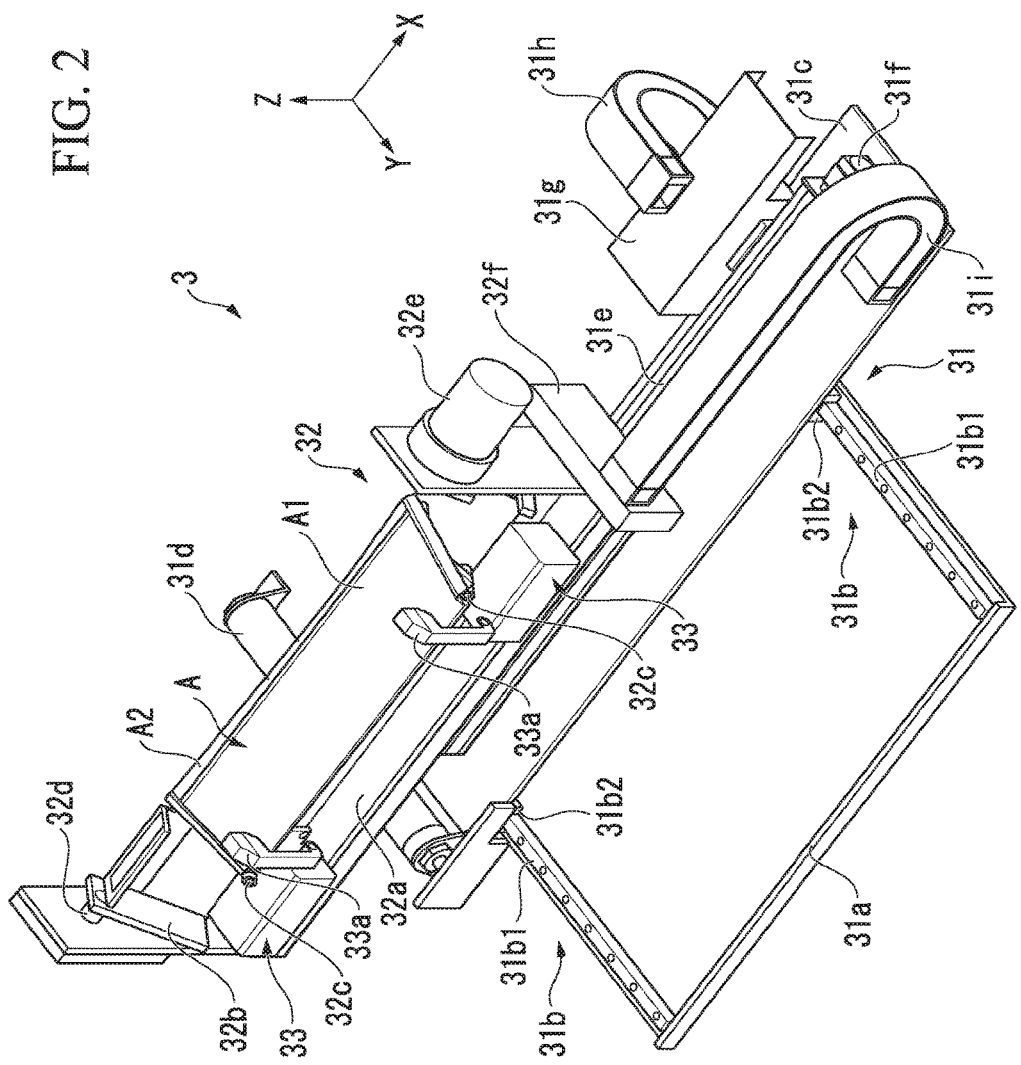
FIG. 2 is a perspective view of a moving apparatus included in the non-destructive inspection apparatus according to the embodiment of the present disclosure.
Figure 3:
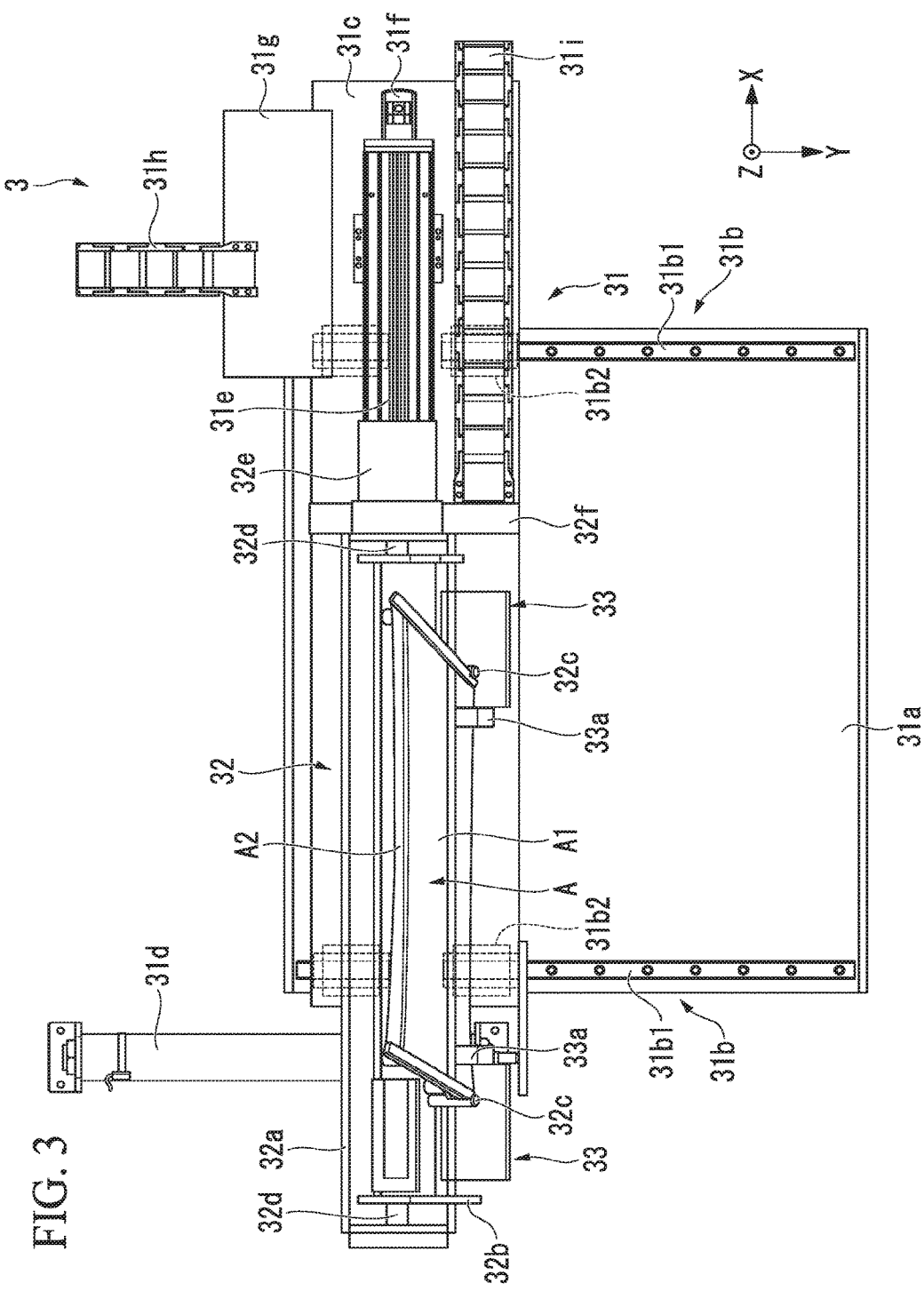
FIG. 3 is a plan view of the moving apparatus included in the non-destructive inspection apparatus according to the embodiment of the present disclosure.
Figure 4:
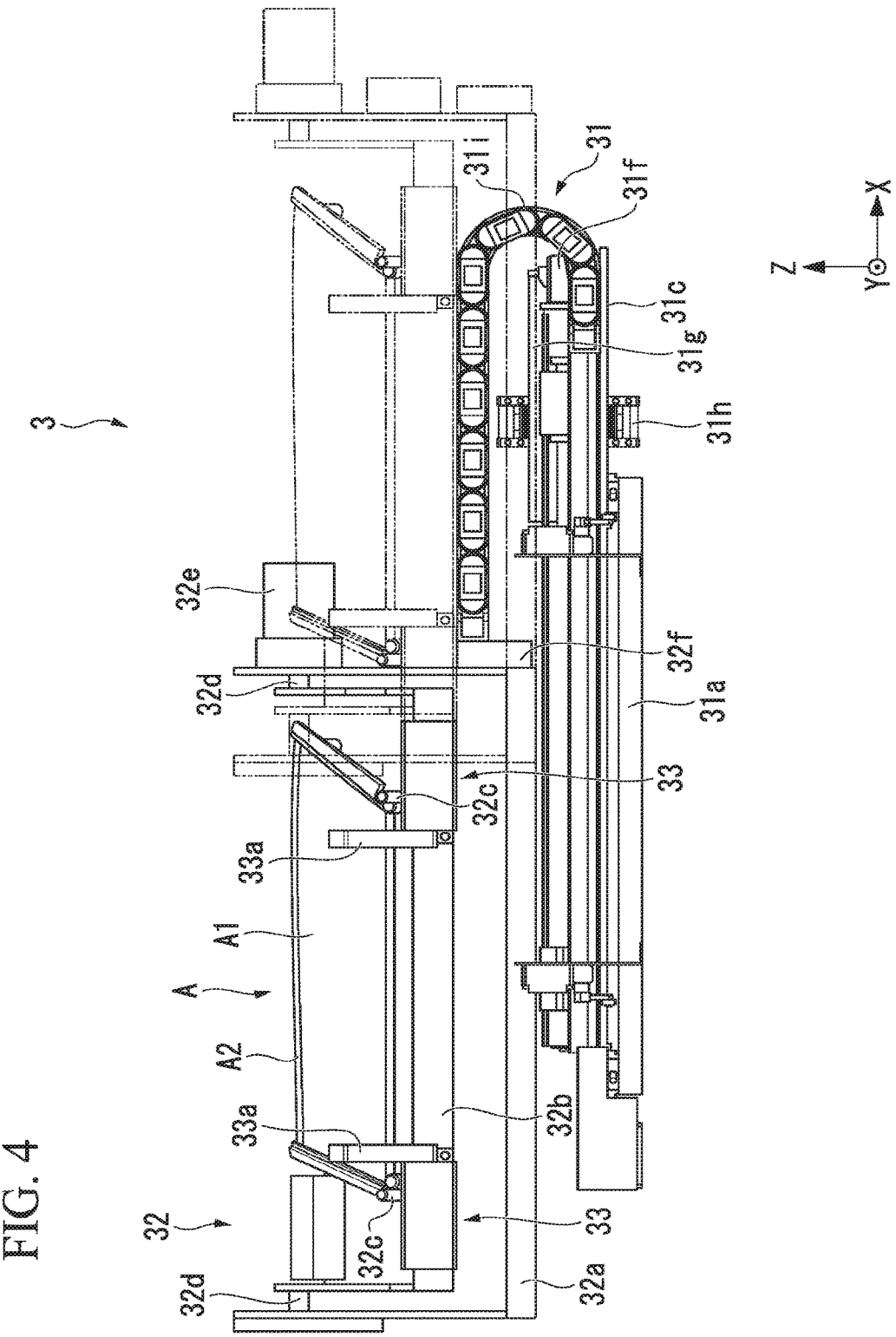
FIG. 4 is a front view of the moving apparatus included in the non-destructive inspection apparatus according to the embodiment of the present disclosure.

FIG. 2 is a perspective view of the moving apparatus 3. FIG. 3 is a plan view of the moving apparatus 3. FIG. 4 is a front view of the moving apparatus 3. As shown in FIGS. 2 to 4, the moving apparatus 3 includes a stage apparatus 31, an inversion apparatus 32 and clamp units 33.

The stage apparatus 31 includes a base 31a, advance/retreat guides 31b, a moving stage 31c, an advance/retreat cylinder 31d, a traversing guide 31e, a traversing pulse motor 31f, a driver unit 31g, a first cable unit 31h and a second cable unit 31i.

The base 31a is accommodated in the housing 2 and fixed to a floor section of the housing 2. The base 31a directly or indirectly supports the advance/retreat guides 31b, the moving stage 31c, the traversing guide 31e, the traversing pulse motor 31f, the driver unit 31g, the first cable unit 31h and the second cable unit 31i, as well as the inversion apparatus 32 and the clamp units 33.

The advance/retreat guides 31b are a pair of linear motion (LM) guides installed on the base 31a. The advance/retreat guides 31b have guide rails 31b1 installed to extend in a forward/backward direction (a Y direction), and movers 31b2 movable on the guide rails 31b1. The movers 31b2 are slidably fitted onto the guide rails 31b1 serving as stators, and movable along the guide rails 31b1 in the forward/backward direction (the Y direction). The advance/retreat guides 31b are installed at end portions of the base 31a in a leftward/rightward direction (an X direction). The moving stage 31c is a flat plate-shaped stage that is fixed to the movers 31b2 of the advance/retreat guides 31b to be movable in the forward/backward direction (the Y direction). The moving stage 31c directly supports the traversing guide 31e, the traversing pulse motor 31f, the driver unit 31g and the second cable unit 31i.

The advance/retreat cylinder 31d is disposed behind the base 31a and fixed to the floor section of the housing 2. The advance/retreat cylinder 31d has a rod that is movable in the forward/backward direction (the Y direction), and a tip of the rod is fixed to the moving stage 31c.

The advance/retreat cylinder 31d is electrically connected to the control unit 8 and moves the moving stage 31c in the forward/backward direction (the Y direction) under control of the control unit 8.

The traversing guide 31e is a linear motion (LM) guide installed on the moving stage 31c. The traversing guide 31e has a guide rail installed to extend in the leftward/rightward direction (the X direction), and a mover that is movable on the guide rail. The traversing pulse motor 31f is disposed at a right side of the traversing guide 31e and fixed to the moving stage 31c. The traversing pulse motor 31f is connected to the control unit 8 via the driver unit 31g and the first cable unit 31h and moves the mover of the traversing guide 31e in the leftward/rightward direction (the X direction) under control of the control unit 8.

The driver unit 31g is disposed behind the traversing guide 31e and fixed to the moving stage 31c. The driver unit 31g is connected to the traversing pulse motor 31f and further connected to the control unit 8 via the first cable unit 31h. The driver unit 31g drives the traversing pulse motor 31f based on an instruction input from the control unit 8. The second cable unit 31i connects the moving stage 31c and a driver unit 32f (to be described below) of the inversion apparatus 32 and connects the control unit 8 and the driver unit 32f of the inversion apparatus 32 via the driver unit 31g and the first cable unit 31h.

The stage apparatus 31 moves the guide vane A supported by the clamp units 33 in the forward/backward and leftward/rightward directions (the X-Y directions), i.e., a horizontal direction, under control of the control unit 8.

The inversion apparatus 32 includes a base frame 32a, a pivot frame 32b, positioning pins 32c, rotary shaft sections 32d, a servo motor 32e and the driver unit 32f.

The base frame 32a is fixed to the mover of the traversing guide 31e included in the stage apparatus 31 and therefore is movable in the leftward/rightward direction (the X direction). The base frame 32a rotatably supports the pivot frame 32b via the rotary shaft sections 32d. The pivot frame 32b is a portion on which the guide vane A is directly placed. The pivot frame 32b is installed to be rotatable with respect to the base frame 32a about an axis in the leftward/rightward direction defined by the rotary shaft sections 32d.

The plurality of positioning pins 32c are vertically installed at the pivot frame 32b to protrude from the pivot frame 32b. The positioning pins 32c are disposed at positions corresponding to a common shape portion of the guide vane A. That is, the non-destructive inspection apparatus 1 of the embodiment inspects, as inspection targets, various kinds of guide vanes having different shapes as well as one kind of guide vane A. The guide vanes serving as the inspection targets have common shapes, although the exact shapes are different from each other. The plurality of positioning pins 32c are disposed to abut portions having the above-mentioned common shapes (i.e., common shape portions).

According to the positioning pins 32c, regardless of the shapes of the guide vanes, as long as they are the guide vanes serving as inspection targets, the guide vanes can be disposed at reference positions to perform non-destructive inspection as the common shape portions are disposed to abut the positioning pins 32c. That is, in the embodiment, as the guide vane A is placed on the pivot frame 32b such that the common shape portion abuts the positioning pins 32c, the guide vane A is disposed at the reference position.

The rotary shaft sections 32d are installed at both ends of the pivot frame 32b in the leftward/rightward direction (the X direction) and pivotally support the pivot frame 32b with respect to the base frame 32a. The rotary shaft sections 32d are disposed in the vicinity of a front edge, which serves as an inspection target place, of the guide vane A in an upward/downward direction (a Z direction) and pivot the guide vane A about the vicinity of the front edge when the pivot frame 32b is pivoted.

The servo motor 32e is fixed to the base frame 32a so as to be connected to one of the rotary shaft sections 32d and generates a driving force to pivot the pivot frame 32b. The pivot frame 32b is pivoted as the driving force generated by the servo motor 32e is transmitted to the pivot frame 32b via the rotary shaft section 32d. The driver unit 32f is disposed under the servo motor 32e and fixed to the base frame 32a. The driver unit 32f is connected to the servo motor 32e and further connected to the second cable unit 31i. The driver unit 32f is connected to the control unit 8 via the second cable unit 31i and drives the servo motor 32e based on an instruction input from the control unit 8.

Figure 5A:
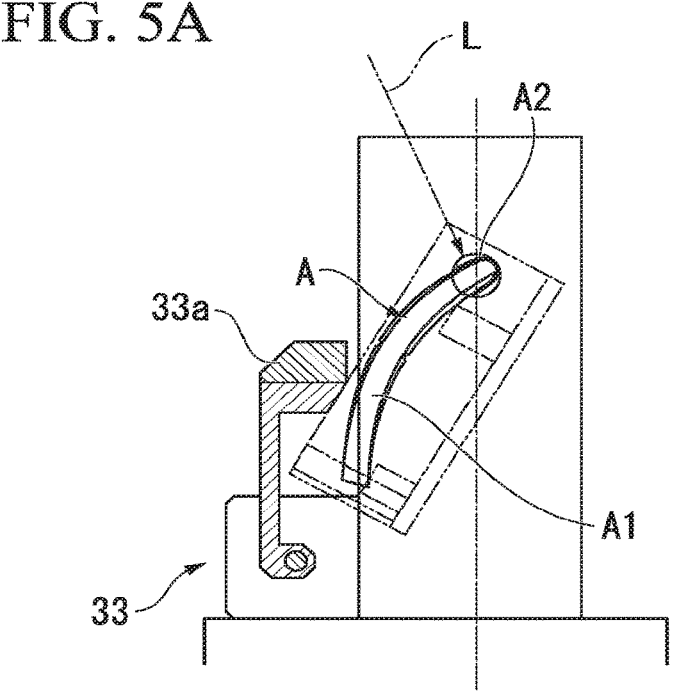
FIG. 5A is a schematic diagram showing an aspect of inversion of a guide vane by the moving apparatus included in the non-destructive inspection apparatus according to the embodiment of the present disclosure.
Figure 5B:
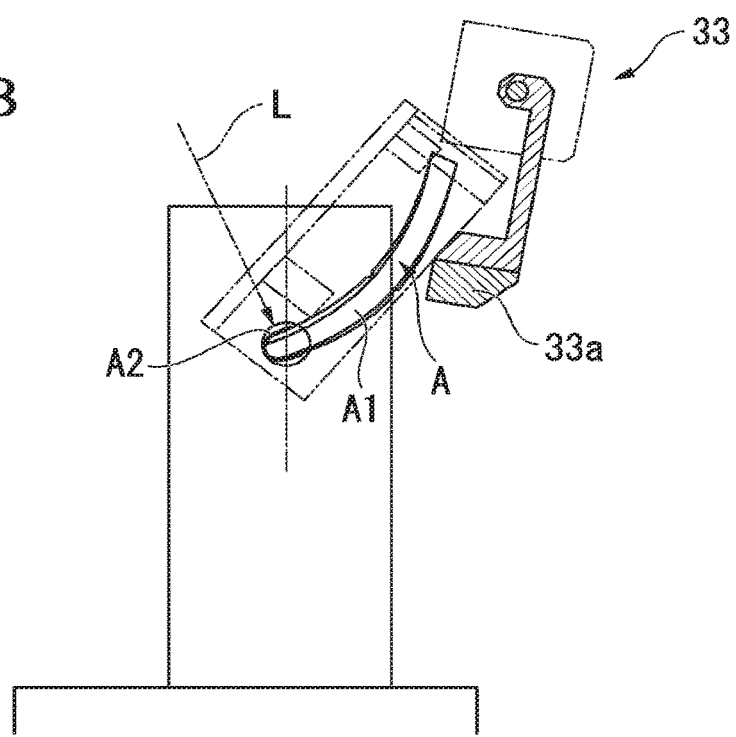
FIG. 5B is a schematic diagram showing the aspect of inversion of the guide vane by the moving apparatus included in the non-destructive inspection apparatus according to the embodiment of the present disclosure.

The inversion apparatus 32 pivots the pivot frame 32b, to which the guide vane A is fixed by the clamp units 33, around an X axis (an axis in the leftward/rightward direction) under control of the control unit 8. For example, the inversion apparatus 32 inverts the guide vane A fixed by the clamp units 33 with respect to a laser beam L (i.e., the laser beam source apparatus 4 shown in FIG. 1) as shown in FIGS. 5A and 5B by inverting the pivot frame 32b by about 180° using the servo motor 32e. In addition, the inversion apparatus 32 adjusts a position of the guide vane A in the upward/downward direction (the Z direction) by slightly pivoting the servo motor 32e.

The clamp units 33 are installed with respect to the pivot frame 32b of the inversion apparatus 32 and disposed at both ends of the pivot frame 32b in the leftward/rightward direction (the X direction). The clamp units 33 include clamps 33a pivoted by a hydraulic unit electrically connected to the control unit 8. The guide vane A placed on the pivot frame 32b is fixed by the clamps 33a.

Returning to FIG. 1, the laser beam source apparatus 4 is disposed above the moving apparatus 3 and radiates a laser beam toward the moving apparatus 3. The laser beam is selected to have an output that can sufficiently heat the guide vane A without a black body tape or black body paint being applied. The laser beam source apparatus 4 has a homogenizer, and a radiation spot of the laser beam is adjusted in a rectangular shape.

The infrared camera 5 is disposed in the vicinity of the laser beam source apparatus 4 and supported in the housing 2 by a support section (not shown). The infrared camera 5 images the front edge and its vicinity of the guide vane A to obtain imaging data and outputs the imaging data toward the control unit 8. In the embodiment, an imaging range of the infrared camera 5 is smaller than a length of the guide vane A in the leftward/rightward direction (the X direction) (a length of the guide vane A in a height direction). For this reason, in the embodiment, the guide vane A is imaginarily divided into a plurality of imaging regions in the leftward/rightward direction (the X direction), imaging data of each of the imaging regions is imaged by the infrared camera 5, the imaging data is synthesized by the control unit 8, and thus the imaging data of the entire region of the guide vane A in the leftward/rightward direction (the X direction) is acquired.

The curtain sensor 6 is installed at the opening section of the housing 2, detects whether an operator or the like is present and outputs the detected result to the control unit 8. In case where the operator is detected upon driving of the moving apparatus 3 or injection of a laser beam, an operation of the non-destructive inspection apparatus 1 is stopped by the control unit 8.

The manipulation monitor 7 is a man-machine interface attached to an outer wall surface of the housing 2. The manipulation monitor 7 includes, for example, a touch panel sensor and outputs an instruction input by an operator to the control unit 8. In addition, the manipulation monitor 7 visualizes and displays information input from the control unit 8. For example, the manipulation monitor 7 displays an inspection result input from the control unit 8.

The control unit 8 controls the entire operation of the non-destructive inspection apparatus 1 of the embodiment. In the embodiment, the control unit 8 stores a program for generating an image showing a bonded state of a bonded place of the guide vane A based on the imaging data and obtains an image and a determination result showing the bonded state based on the imaging data input from the infrared camera 5. Here, the control unit 8 performs inspection regardless of the temperature of the guide vane A by measuring a phase change using a so-called DFT (a kind of FET). Note that a specific method of obtaining a bonded state from the imaging data is exemplarily disclosed in the above-mentioned Patent Documents, and a detailed description thereof will be omitted.

The control unit 8 of the embodiment previously stores form data of the guide vane A. The control unit 8 controls the moving apparatus 3 such that the bonded place of the guide vane A is placed at a radiation region of a laser beam and further the plurality of imaging regions are matched to the imaging range of the infrared camera 5. That is, the control unit 8 stores form data of the guide vane A and controls the moving apparatus 3 such that a laser beam is radiated to the bonded place of the guide vane A based on the form data. Further, the control unit 8 controls the moving apparatus 3 such that the bonded place of the guide vane A is imaged by the infrared camera 5 based on the form data.

The guide vane A serving as the inspection target in the embodiment is formed by bonding a bonding material A2 formed of a metal material to a front edge and its vicinity of a base material A1 having a blade shape and formed of a fiber-strengthened material (for example, CFRP) including a carbon fiber and the like. The bonding material A2 is formed to a portion from a positive pressure surface side to a negative pressure surface side of the base material A1 including the front edge. The bonded place between the base material A1 and the bonding material A2 of the guide vane A is a place at which the bonded state is inspected by the non-destructive inspection apparatus 1 of the embodiment. When the common shape portion is disposed to abut the positioning pins 32c as described above, as shown in FIGS. 2 to 4, the guide vane A is disposed such that the bonded place (i.e., a front edge portion) between the base material A1 and the bonding material A2 is directed toward a rear upper side and a rear edge portion is directed toward a front lower side.

In the non-destructive inspection apparatus 1 of the embodiment having the above-mentioned configuration, when the guide vane A is installed on the pivot frame 32b such that the common shape portion abuts the positioning pins 32c and an instruction showing start is input into the manipulation monitor 7 by an operator, the control unit 8 fixes the guide vane A to the clamp units 33 using the clamps 33a.

Next, the control unit 8 moves the guide vane A into the housing 2 using the moving apparatus 3 and closes the shutter 2a. Further, the control unit 8 moves the guide vane A to an initial position of inspection start using the moving apparatus 3 based on the form data. The initial position disclosed herein is a position (shown in FIG. 5A) at which a right (+X side) end portion of the negative pressure surface side of the bonded place of the guide vane A is irradiated with the laser beam emitted from the laser beam source apparatus 4. At this time, the imaging range of the infrared camera 5 overlaps the imaging region disposed at the rightmost side (the +X side) among the plurality of imaging regions. Then, the control unit 8 emits a laser beam from the laser beam source apparatus 4, heats an end portion of the bonded place, images the bonded place using the infrared camera 5 for a time from heating start to lapse of a certain time after heating and acquires imaging data.

Figure 6:
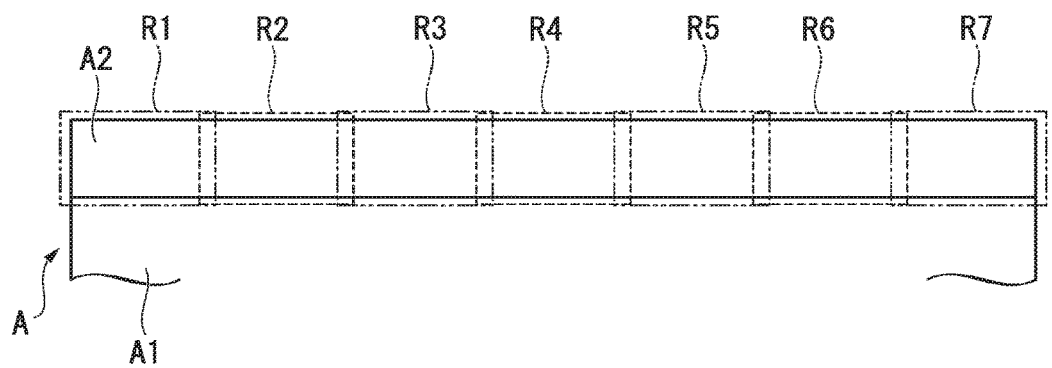
FIG. 6 is a view for describing imaging regions in the non-destructive inspection apparatus according to the embodiment of the present disclosure.

Here, in the embodiment, as shown in FIG. 6, the negative pressure surface side of the bonded place of the guide vane A is divided into seven imaging regions (imaging regions R1 to R7) in the height direction (the leftward/rightward direction of FIG. 6) of the guide vane A. Further, as shown in FIG. 6, the neighboring imaging regions are disposed to partially overlap each other. That is, in the embodiment, the bonded place is divided into a plurality of imaging regions, in which the neighboring imaging regions partially overlap each other.

When the imaging data of the imaging region R1 is obtained in the previous imaging, the control unit 8 moves the guide vane A using the moving apparatus 3 based on the form data such that the imaging range of the infrared camera 5 and the radiation spot of the laser beam overlap the imaging region R2. Then, the control unit 8 acquires the imaging data of the imaging region R2 through imaging by the infrared camera 5 after the laser beam is radiated to the imaging region R2 for a constant time from the laser beam source apparatus 4. As the above-mentioned operation is repeated, the control unit 8 acquires the imaging data of all of the imaging regions R1 to R7.

When the imaging data of the imaging regions R1 to R7 is obtained, as shown in FIG. 5B, the control unit 8 inverts the guide vane A with respect to the laser beam L using the inversion apparatus 32. The positive pressure surface side of the bonded place of the guide vane A is also divided into seven imaging regions, in which the neighboring imaging regions partially overlap each other. Then, the control unit 8 acquires the imaging data of all of the imaging regions of the positive pressure surface side of the bonded place of the guide vane A.

When the imaging data of the entire bonded place of the guide vane A is acquired in this way, the control unit 8 generates an image showing a bonded state from the imaging data while synthesizing the imaging data as a whole and performs determination of the bonded state according to necessity. Then, the control unit 8 displays the image showing the bonded state and determination result of the bonded state on the manipulation monitor 7.

In addition, simultaneously, the control unit 8 moves the guide vane A to the outside of the housing 2 using the moving apparatus 3 and releases the clamps 33a of the clamp units 33.

According to the non-destructive inspection apparatus 1 of the above-mentioned embodiment, since the laser beam having a higher energy density than a flashlamp is radiated to the bonded place of the guide vane A, non-destructive inspection can be performed without applying a black body tape or black body paint. In addition, the control unit 8 that stores the form data of the guide vane A controls the moving apparatus 3 configured to move the guide vane A so that the laser beam is radiated to the bonded place. Accordingly, the various kinds of guide vanes having complex shapes can be easily inspected. In this way, according to the non-destructive inspection apparatus 1 of the embodiment, the guide vane A having a complex shape can be easily inspected without applying the black body tape or the black body paint, and the bonded state can be obtained in a short time.

In addition, in the non-destructive inspection apparatus 1 of the embodiment, the moving apparatus 3 includes the stage apparatus 31 configured to move the guide vane A in the horizontal direction, and the inversion apparatus 32 configured to invert the guide vane A with respect to the laser beam source apparatus 4. For this reason, according to the non-destructive inspection apparatus 1 of the embodiment, the bonded place of the guide vane A can be moved to an arbitrary place, a laser beam can be reliably radiated to the bonded place, and the imaging data of the bonded place can be reliably acquired.

In addition, according to the non-destructive inspection apparatus 1 of the embodiment, the moving apparatus 3 has the plurality of positioning pins 32c disposed at positions abutting the common shape portions of the plurality of guide vanes A having different shapes and configured to perform positioning of the guide vanes A. For this reason, according to the non-destructive inspection apparatus 1 of the embodiment, the guide vanes A can easily be disposed at reference positions for performing the inspection.

In addition, according to the non-destructive inspection apparatus 1 of the embodiment, the control unit 8 is configured to acquire imaging data of the whole of the bonded place by dividing the bonded place of the guide vane A into a plurality of imaging regions, in which the neighboring imaging regions partially overlap each other, to be imaged by the infrared camera. For this reason, occurrence of a region in which the imaging data is not acquired between the imaging regions can be prevented and the imaging data of the whole of the bonded place can be reliably acquired.

Hereinabove, while the exemplary embodiment of the present disclosure has been described with reference to the accompanying drawings, it is needless to say that the present disclosure is not limited to the embodiment. All shapes or combinations of the components shown in the above-mentioned embodiment are exemplarily provided, and various modifications may be made based on design requirements or the like without departing from the spirit of the present disclosure.

In the embodiment, the gas turbine engine parts in the present disclosure have been exemplarily described as the guide vanes A. However, the present disclosure is not limited thereto but gas turbine engine parts other than the guide vanes A may also be inspection targets as long as the parts are formed by bonding a bonding material formed of a metal material to a base material formed of a fiber-strengthened material.

For example, a fan blade or a fan case may also be an inspection target.

INDUSTRIAL APPLICABILITY

According to the present disclosure, in the non-destructive inspection of a bonded place of a gas turbine engine part in which a bonding material formed of a metal material is bonded to a base material formed of a fiber-strengthened material, various kinds of gas turbine engine parts having complex shapes can be easily inspected without applying a black body tape or black body paint.

What is claimed is:

1. A non-destructive inspection apparatus configured to perform non-destructive inspection of a bonded place between a base material and a bonding material of a gas turbine engine part, the gas turbine engine part being formed by bonding the bonding material formed of a metal material to the base material formed of a fiber-strengthened material, the non-destructive inspection apparatus comprising:
- a moving apparatus configured to move the gas turbine engine part;
- a light source apparatus configured to emit a laser beam;
- an infrared imaging apparatus configured to image the gas turbine engine part to which the laser beam is radiated; and
- a control and arithmetic processing apparatus configured to store form data of the gas turbine engine part, control the moving apparatus such that the laser beam is radiated to the bonded place based on the form data, and obtain a result showing a state of the bonded place based on imaging data obtained by the infrared imaging apparatus, wherein the moving apparatus includes:
- a stage apparatus configured to move the gas turbine engine part in a horizontal direction; and
- an inversion apparatus including a pivot frame to which the gas turbine engine part is fixed and which is rotatable about an axis parallel to the horizontal direction, and configured to invert the gas turbine engine part with respect to the light source apparatus by inverting the pivot frame.

2. The non-destructive inspection apparatus according to claim 1, wherein the moving apparatus has positioning pins disposed at positions abutting common shape portions of a plurality of gas turbine engine parts having different shapes and configured to perform positioning of the gas turbine engine parts.

3. The non-destructive inspection apparatus according to claim 1, wherein the control and arithmetic processing apparatus is configured to acquire imaging data of a whole of the bonded place by dividing the bonded place into a plurality of imaging regions, in which neighboring imaging regions partially overlap each other, to be imaged by the infrared imaging apparatus.

4. The non-destructive inspection apparatus according to claim 2, wherein the control and arithmetic processing apparatus is configured to acquire imaging data of a whole of the bonded place by dividing the bonded place into a plurality of imaging regions, in which neighboring imaging regions partially overlap each other, to be imaged by the infrared imaging apparatus.

5. The non-destructive inspection apparatus according to claim 1, wherein the gas turbine engine part is a blade.

* * * * *